United States Patent [19]
Lenker et al.

[11] Patent Number: 6,131,575
[45] Date of Patent: *Oct. 17, 2000

[54] URINARY INCONTINENCE DEVICE

[75] Inventors: Jay Lenker, Palo Alto; Robert Rosenbluth, Laguna Niguel; Brian Cox, Lake Forest; George R. Greene, Costa Mesa, all of Calif.

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/673,174

[22] Filed: Jun. 26, 1996

Related U.S. Application Data

[63] Continuation of application No. 08/286,934, Aug. 8, 1994, abandoned, which is a continuation-in-part of application No. 07/810,845, Dec. 20, 1991, Pat. No. 5,336,208, which is a continuation-in-part of application No. 07/639,921, Jan. 10, 1991, Pat. No. 5,074,855.

[51] Int. Cl.⁷ ...................................................... A61F 5/48
[52] U.S. Cl. ................................... 128/885; 128/DIG. 25; 600/29
[58] Field of Search ...................................... 604/349, 352, 604/355; 128/842–844, 893, 894, 887, 885, DIG. 25; 602/48, 58; 24/DIG. 11; 427/443, 448, 449; 600/29

[56] References Cited

U.S. PATENT DOCUMENTS

| | | |
|---|---|---|
| 678,943 | 7/1901 | Davis . |
| 2,548,149 | 4/1951 | Fowler . |
| 2,649,854 | 8/1953 | Salm . |
| 2,891,546 | 6/1959 | Galloway . |
| 2,938,519 | 5/1960 | Marco . |
| 3,463,141 | 8/1969 | Mozolf . |
| 3,677,250 | 7/1972 | Thomas ........................... 24/DIG. 11 |
| 3,905,372 | 9/1975 | Denkinger . |
| 4,197,849 | 4/1980 | Bostick . |
| 4,365,621 | 12/1982 | Brundin . |
| 4,419,097 | 12/1983 | Rowland . |
| 4,445,900 | 5/1984 | Roeder ................................... 604/389 |
| 4,576,599 | 3/1986 | Lipner ..................................... 604/389 |
| 4,578,065 | 3/1986 | Habib ...................................... 604/336 |

(List continued on next page.)

FOREIGN PATENT DOCUMENTS

| | | | |
|---|---|---|---|
| 674811 | 11/1963 | Canada ................................. 128/893 |
| 0 407 218 A1 | 1/1991 | European Pat. Off. . |
| 433954 | 8/1935 | United Kingdom ................... 128/893 |
| 0 557 677 | 9/1993 | United Kingdom . |

*Primary Examiner*—Mark O. Polutta

[57] ABSTRACT

A device for managing urinary incontinence comprises a resilient body that engages the external genitalia and sealingly occludes the urethral meatus. In female embodiments, the body fits between the labia minora and the floor of the vulval vestibule, occluding the meatus. An adhesive on the body provides a sealing engagement with the meatus. In a first female embodiment, the body has a base with an adhesive layer that seats against the vestibule floor. A pair of flexible, lateral flaps engage the labia minora. A layer of super-absorbent material may be situated between the base and the adhesive layer, and/or a layer of scrim material may be so situated. The body may have a longitudinal ridge with a posterior edge having a finger hole to facilitate installation and removal of the device. In a second female embodiment, the body is substantially tubular, with the adhesive on the exterior surface of the body. In a third female embodiment, the body is an elastomeric bladder, filled with a liquid or gel, that conformingly fits between the labia minora and the vestibule floor so as to occlude the meatus. The exterior surface of the bladder is coated with an adhesive to sealingly occlude the meatus. In male embodiments, the device includes a resilient pad with adhesive on one surface. The pad conforms to and adhesively attaches to the penile glans, with the adhesive sealingly occluding the meatus. Securing tabs may be provided to adhere to the glans or the penile shaft.

15 Claims, 4 Drawing Sheets

U.S. PATENT DOCUMENTS

| | | | |
|---|---|---|---|
| 4,638,790 | 1/1987 | Conway et al. | |
| 4,640,688 | 2/1987 | Hauser. | |
| 4,731,064 | 3/1988 | Heyden | 604/352 |
| 4,790,835 | 12/1988 | Elias | 604/349 |
| 4,821,742 | 4/1989 | Phelps, III. | |
| 4,846,909 | 7/1989 | Klug et al. | |
| 4,863,448 | 9/1989 | Berg | 604/349 |
| 4,880,016 | 11/1989 | Worth et al. | |
| 4,909,244 | 3/1990 | Quarfoot et al. | 602/48 |
| 4,920,986 | 5/1990 | Biswas. | |
| 4,971,074 | 11/1990 | Hrubetz | 128/885 |
| 4,981,465 | 1/1991 | Ballan et al. | |
| 5,009,224 | 4/1991 | Cole. | |
| 5,071,433 | 12/1991 | Naestoft et al. | 623/7 |
| 5,074,855 | 12/1991 | Rosenbluth et al. | 604/385.1 |
| 5,100,396 | 3/1992 | Zamierowski. | |
| 5,114,419 | 5/1992 | Daniel et al. | 604/386 |
| 5,160,341 | 11/1992 | Brenneman et al. | 606/198 |
| 5,184,629 | 2/1993 | Erickson et al. | |
| 5,188,124 | 2/1993 | Feret | 128/893 |
| 5,207,652 | 5/1993 | Kay. | |
| 5,234,409 | 8/1993 | Goldberg et al. | 604/96 |
| 5,263,947 | 11/1993 | Kay | 604/349 |
| 5,334,175 | 8/1994 | Conway et al. | 604/352 |
| 5,336,208 | 8/1994 | Rosenbluth et al. | 604/329 |
| 5,356,372 | 10/1994 | Donovan et al. | 602/58 |
| 5,421,350 | 6/1995 | Friedman. | |
| 5,468,501 | 11/1995 | Kydonieus et al. | 424/443 |
| 5,509,427 | 4/1996 | Simon et al. | 128/DIG. 25 |
| 5,513,660 | 5/1996 | Simon et al. | 128/DIG. 25 |
| 5,630,429 | 5/1997 | Dann. | |
| 5,662,926 | 9/1997 | Wick et al. | 424/448 |
| 5,746,222 | 5/1998 | Simon et al. | 128/DIG. 25 |
| 5,752,525 | 5/1998 | Simon et al. | 128/DIG. 25 |
| 5,769,091 | 6/1998 | Simon et al. | 128/DIG. 25 |

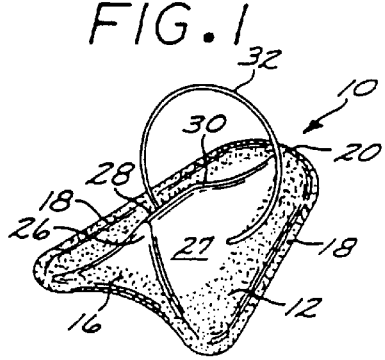
FIG. 1
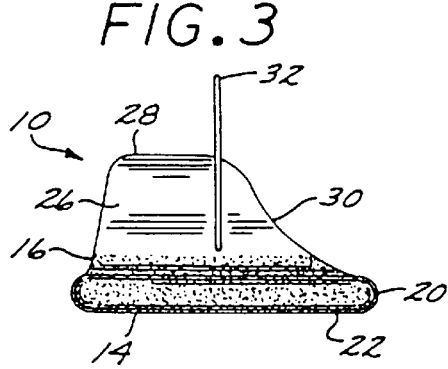
FIG. 3
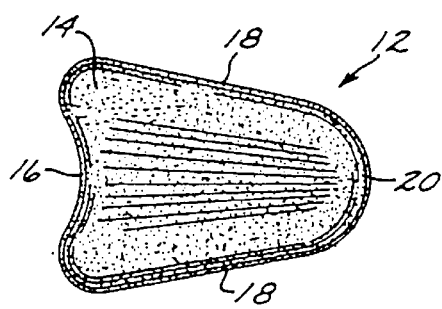
FIG. 2
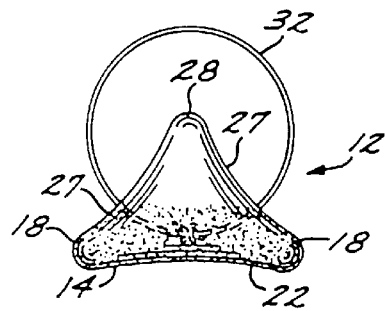
FIG. 4
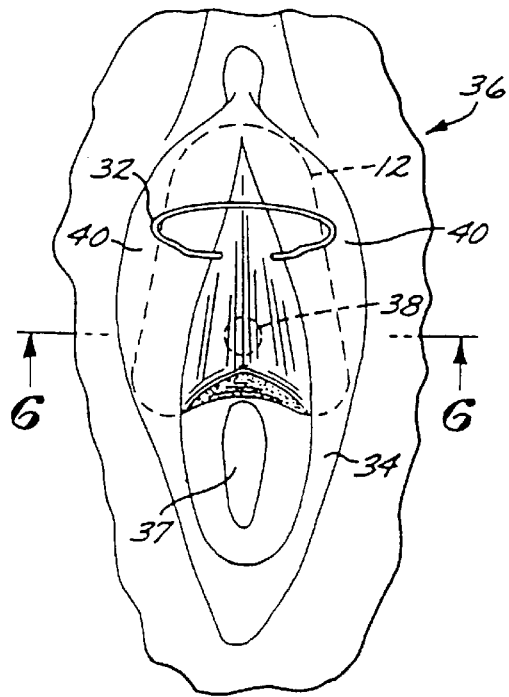
FIG. 5
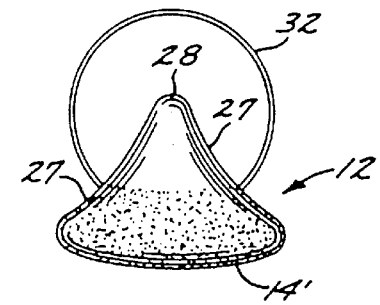
FIG. 7
FIG. 6

URINARY INCONTINENCE DEVICE

CROSS-REFERENCE TO RELATED APPLICATIONS

This is a continuation of application Ser. No. 08/286,934, filed Aug. 8, 1994, now abandoned, which is a continuation-in-part of Ser. No. 07/810,845, filed Dec. 20, 1991, now U.S. Pat. No. 5,336,208, which is a continuation-in-part of Ser. No. 07/639,921, filed Jan. 10, 1991, now U.S. Pat. No. 5,074,855.

BACKGROUND OF THE INVENTION

This invention relates to the field of devices or appliances used to relieve or mitigate the problems associated with human urinary incontinence. More specifically, the present invention relates to a removable external closure for the human urethra.

Urinary incontinence, due to disease, injury, or other causes, is a troublesome problem for many individuals. Surgical intervention is often required to treat severe cases of incontinence, but in those cases where the patient suffers from only a partial loss of bladder control, or where the patient is otherwise a poor candidate for surgery, nonsurgical treatment is called for. While both male and female patients may be good candidates for nonsurgical treatment, such nonsurgical approaches are particularly appropriate for female patients who suffer from the partial, sporadic loss of bladder control sometimes referred to as "stress incontinence" or "urge incontinence". Such stress or urge incontinence, in fact, is the most common cause of urine loss in adult women.

Nonsurgical management of urinary incontinence includes non-therapeutic management, wherein the patient wears an appliance or device proximate the urethral orifice ("meatus") that collects or captures urinary discharge. Such devices fall generally into two categories: (1) urine collection devices, and (2) absorbent pads.

Urine collection devices typically comprise a receiving orifice or receptacle for capturing urine flowing from the urethra; retention means, associated with the receptacle or orifice, for holding the receptacle or orifice in the proximity of the urethral meatus; and means for directing urine from the receptacle or orifice to a reservoir or a container or the like for disposal. Devices of this general description, for use by female patients, are disclosed in the following U.S. Pat. No. 3,512,185—Ellis; U.S. Pat. No. 3,661,155—Lindan; U.S. Pat. No. 4,412,511—Steer et al.; U.S. Pat. No. 4,457,314—Knowles; U.S. Pat. No. 4,484,917—Blackmon; U.S. Pat. No. 4,690,677—Erb; U.S. Pat. No. 4,822,347—MacDougall; and U.S. Pat. No. 4,846,819—Welch. A variation on the urinary collection device theme is the "female external catheter", disclosed in U.S. Pat. No. 4,563,183—Barrodale et al., which includes a catheter tube having one end inserted into the urethra. In many of these devices, the retention means are configured so as to be inserted into the interlabial space, being retained therein by the anatomical structure of the external female genitalia. The Blackmon and MacDougall devices also use an adhesive to assist in retention.

The category of absorbent pads includes a wide variety of devices, primarily for use by female patients, which generally comprise a body of absorbent material configured so as to be insertable into the interlabial space, and retained therein by the anatomical structure of the external female genitalia. Such devices typically resemble (and, indeed, can function as) catamenial sanitary napkins. The following U.S. Patents disclose devices that may generally be considered within this category: U.S. Pat. No. 3,983,873—Hirschman; U.S. Pat. No. 4,595,392—Johnson et al.; U.S. Pat. No. 4,627,848—Lassen et al.; U.S. Pat. No. 4,673,403—Lassen et al.; U.S. Pat. No. 4,743,245—Lassen et al.; U.S. Pat. No. 4,804,380—Lassen et al.; and U.S. Pat. No. 4,846,824—Lassen et al. A sanitary napkin that is configured for interlabial retention, and that could be used to capture and absorb urine flow, is disclosed in British Patent No. 754,481.

While the above-described devices are useful in certain applications, they are subject to a number of disadvantages. For example, the urine collection devices require the user to wear a reservoir or container that may be prone to overflow or spillage. Also, such devices are better suited to users who suffer from chronic or severe loss of bladder function, rather than those who suffer only from moderate stress or urge incontinence. The absorbent pads tend to be bulky, and may be uncomfortable for some users, especially when wet. Odor associated with urine collection devices is often noticeable by others, and is therefore undesireable.

Use of the prior art devices described above is based upon the assumption that the flow of urine out of the urethra cannot or should not be stopped. This assumption may not be true in many cases of stress or urge incontinence, which are transient in nature. In such cases, external occlusion of the urethral meatus may provide an adequate degree of continence for many patients, but this approach has been overlooked, at least for the most part, by the prior art.

There is, therefore, a need for a device that provides for the effective management of urinary incontinence by means of the external occlusion of the urethral meatus; that is easy to use and comfortable to wear; and that provides for secure retention with good sealing qualities.

SUMMARY OF THE INVENTION

Broadly, the present invention is a urethral meatus occlusion device, comprising a resilient body, configured to engage and seal against the urethral meatus, and to be retained in place by engagement with the anatomical structure of the external genitalia. More specifically, in one preferred female embodiment, the body is a pad that includes a base, having a substantially triangular or arrowhead-shaped outline, that is adapted to seat against the vestibule of the vulva, anteriorly of the vaginal orifice, thereby occluding the urethral meatus. The lateral edges of the pad are configured to fit inside the labia minora, the engagement between the pad and the labia thereby retaining the pad firmly against the vestibule, in sealing engagement against the meatus. The side of the pad opposite the base is configured with a central longitudinal ridge that, when the pad is installed in the vestibule, extends into the interlabial space. A loop of thread may be inserted through the ridge to facilitate removal of the device, or a finger hole may be provided into the posterior of the ridge for the same purpose.

In a second preferred female embodiment of the invention, the pad has a substantially tubular configuration, and thus lacks the lateral edges or "wings" of the first preferred female embodiment. This "wingless" embodiment is adapted for use where the floor of the vestibule is narrower than what may be considered "normal". As with first preferred female embodiment, the pad seats against the floor of the vestibule, anteriorly of the vaginal orifice, thereby occluding the urethral meatus. The tubular portion of the pad is configured to fit inside the labia minora, the engagement between the pad and the labia thereby retaining the pad firmly against the vestibule, in sealing engagement against the meatus. The side of the pad opposite the base is configured with a central longitudinal ridge that, when the pad is installed in the vestibule, extends into the interlabial space, thereby facilitating insertion and removal.

In both of the aforementioned embodiments, at least that portion of the pad that lies in sealing engagement against the meatus is coated with a pressure-sensitive, hydrophilic hydrogel adhesive for retention against the vestibule. The adhesive, in concert with the resilient pad, spreads to fill the interlabial space proximate the vestibule, thereby providing a conformal fit with the anatomical structure, which enhances the retention of the device. The pad itself can be coated or impregnated with a suitable anti-bacterial or germicidal agent to inhibit infection.

In a third preferred female embodiment of the invention, the body comprises an elastomeric bladder or sac, filled with a soft, compliant, biocompatible gel or liquid, and coated with a pressure-sensitive hydrophilic hydrogel adhesive, to enhance retention. The gel-filled sac spreads within the interlabial space to conform closely to the anatomic structure of the external female genitalia, and thereby seals against the urethral meatus, with the aid of the adhesive.

In several embodiments suitable for use by a male patient, the invention comprises a thin, resilient, absorbent pad, the inner surface of which is provided with a pressure-sensitive hydrophilic hydrogel adhesive layer. The pad conforms to the glans of the penis, and it is removably attached to the penis by means of the adhesive, whereby the adhesive also seals against and occludes the urethral meatus. In one such male embodiment, the pad has a substantially elliptical central portion, with a pair of laterally-extending tabs at each end that are wrapped around the glans for securing the pad in place. In another male embodiment, the pad has a central sealing portion with a plurality of radially-extending tabs for securing the device. In still another male embodiment, the pad is in the configuration of a generally hemispherical cap that covers a substantial portion of the glans. As with the female embodiments, the pad of the male embodiments can be coated or impregnated with a medicinal compound, such as an anti-bacterial or germicidal agent.

It will be appreciated that the present invention offers a new and advantageous approach to the management of incontinence. For example, the device is small, unobtrusive, easy to use, and comfortable to wear. By allowing the user effectively to retain urine, the device avoids the problems associated with prior art devices, enumerated above, that allow the discharge of urine. The device can be made in a variety of sizes and shapes for optimal fit for each individual user. The device is economical to manufacture, and can, therefore, be a disposable item.

These and other advantages will be better appreciated from the detailed description that follows.

BRIEF DESCRIPTION OF THE DRAWINGS

FIG. 1 is a perspective view of a female urinary incontinence device, in accordance with a first preferred female embodiment of the invention;

FIG. 2 is a bottom plan view of the device of FIG. 1;

FIG. 3 is a side elevational view of the device of FIG. 1;

FIG. 4 is an anterior elevational view of the device of FIG. 1;

FIG. 5 is plan view of the device of FIG. 1, showing the device installed in the external genitalia of a human female;

FIG. 6 is a cross-sectional view taken along line 6—6 of FIG. 5;

FIG. 7 is an anterior elevational view of a first modified form of the first preferred female embodiment of the device;

DETAILED DESCRIPTION OF THE INVENTION

Figure 8:
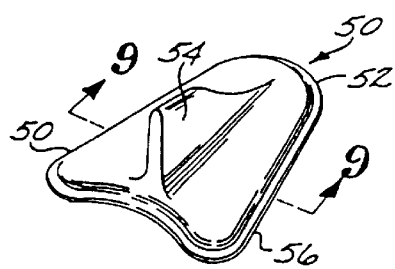
FIG. 8 is a perspective view of a second modified form of the first preferred female embodiment.

Referring first to FIGS. 1 through 4 of the drawings, a female urinary incontinence device 10, in accordance with a first preferred female embodiment of the present invention, is shown. The device comprises a body or pad 12, formed of a resilient foam material that is biocompatible. One suitable class of materials is that of foams formed from the water actuation of prepolymers based on either toluene diisocyanate (TDI) or methylene diphenyl diisocyanate (MDI). Such prepolymers are marketed by W. R. Grace & Co.-Conn., Organic Chemicals Division, Lexington, Massachusetts, under the trademarks "HYPOL" (TDI) and "HYPOL PLUS" (MDI).

Alternatively, the pad 12 can be made of a biodegradable material, such as a cellulose or cotton fiber. A polyurethane foam can also be used, being rendered biodegradable by hydrolysis of a weak backbone link, such as an amine group. Other foam materials, such as polyolefins, can be used and made hydrolytically biodegradable by using weak links such as starches in the polymer backbones.

The pad 12 includes a base 14 that has the general outline of a blunt arrowhead, as shown in FIG. 2. In the first preferred embodiment of the invention, the base may be slightly concave, as shown in FIG. 4. Alternatively, the base 14 can be made slightly convex, as shown in FIG. 7, for those users who might find such a configuration more comfortable to wear. The base 14 has a concave posterior end 16, with lateral edges 18 that taper slightly toward each other as they extend toward a rounded anterior end 20. The anterior end 20 is thus somewhat narrower than the posterior end 16.

The pad is provided with an adhesive surface for retention against the floor of the vestibule. In this embodiment of the invention, the base is coated with an adhesive layer 22, comprising a pressure-sensitive, hydrophilic hydrogel adhesive material. Such hydrogel adhesives are marketed by Promeon Division of Medtronic, Inc., of Minneapolis, Minn., under the trademark "PROMEON". A detailed description of such a hydrogel composition is contained in U.S. Pat. No. 4,593,053—Jevne et al., the disclosure of which is incorporated herein by reference.

Another type of adhesive that has shown good results is a mixture of poly 2-hydroxyethyl methacrylate (PHEMA) and polyethylene glycol (PEG) as a plasticizer. The percentage of PHEMA may range from about 45% to about 75%, with a corresponding range of PEG of about 55% to about 25%. The preferred composition is about 53% to 54% PHEMA and about 47% to 46% PEG. Lower percentages of PHEMA yield greater adhesiveness, while higher percentages of PHEMA yield greater durability. The PEG has a molecular weight between about 400 and about 1000, with 400 preferred. The PHEMA is preferably a mixture of low molecular weight PHEMA (Mw between about 10,000 and about 100,000) and high molecular weight PHEMA (Mw greater than about 100,000). The low Mw PHEMA provides adhesive properties, while the high Mw PHEMA improves adhesive structural integrity. The PHEMA mixture is between about 10%–50% low Mw PHEMA and between about 90% and 50% high Mw PHEMA, with the precise mixture being determined by the particular adhesive properties desired.

While the preferred plasticizer is PEG, as described above, other plasticizers can be used, such as propylene glycol, polypropylene glycol (PPG), or glycerin.

If the pad 12 is made of TDI or MDI, the material of the pad itself can be rendered adhesive by combining the TDI or MDI one-to-one by weight with about 0.25 to 0.50 molar ammonium hydroxide during the water actuation of the foam. The resulting material has a surface that is positively charged, so that it will adhere to a negatively-charged mucoid surface (such as the surface of the vestibule and the inner portions of the labia minora).

Alternatively, the entire pad can be formed of an adhesive, such as the PHEMA/PEG mixture described above.

The side of the pad 12 opposite the base 14 includes a central longitudinal stiffening ridge 26 which forms the thickest part of the pad 12. If one adopts the convention that the base is the "bottom" of the pad 12, then the pad can be defined as having a surface 27 opposite the base that slopes "downwardly" from either side of the ridge 26 toward the edges 18, so that there is a gradual reduction in pad thickness from the ridge to the edges. Viewed another way, the pad can be defined as having a cross-sectional shape that narrows from the base 14 to the "top" or apex 28 of the ridge 26. The resulting configuration is such that a lateral cross section of the pad, taken through the ridge 26, produces a shape resembling a triangle with rounded corners and slightly concave sides, as shown in FIG. 6. Similarly, the ridge 26 has an anterior edge 30 that tapers "downwardly" from the apex 28 toward anterior end 20 of the pad 12, as shown in FIG. 3, so that the anterior end 20 of the pad 12 is substantially reduced in thickness as compared to the posterior end 16.

The device 10 is advantageously provided with a handle or tab that is either integrally molded with the pad 12, or subsequently attached to it. In the first preferred embodiment, handle is a ring or loop 32, preferably of thread, that is inserted laterally through the pad 12. The loop is preferably located near the anterior edge 28 of the ridge 26, although the precise location of the loop 32 is not critical to its function, as will be described below.

FIGS. 5 and 6 show the incontinence device 10 installed in the external genitalia of a human female. The device 10 is installed so that the base 14 is seated against the vestibule 34 of the vulva 36, anteriorly of the vaginal orifice 37, thereby occluding the urethral meatus 38. The adhesive surface seals the meatus sufficiently to prevent the escape of urine. The lateral edges 18 and the anterior end 20 of the pad are tucked under the labia minora 40. The engagement between the labia minora and the sloping surface 27 enhances the retention of the pad 12 in engagement with the vestibule 34. The concavity in the posterior end 16 of the pad 12 allows for somewhat greater surface area for engagement by the labia minora, while leaving a clearance for the vaginal opening 37. The ridge 26 extends into the interlabial space, and the loop 32 protrudes from between the labia majora (not shown), so as to be exposed to facilitate manual grasping, for removal of the device.

The pad 12 can be provided in a number of sizes to fit a large variety of individuals. The length of the pad should be approximately the same as the distance between the anterior lip of the vaginal orifice and the juncture of the labia minora. The width of the pad should optimally conform substantially to the width of the vestibule. Predetermined sizes can be trimmed individually for optimum fit. In some cases, a mold of the relevant portions of the vulva may be taken prior to sizing the pad.

The adhesive layer 22 not only provides a fluid-tight seal for the urethral meatus, but it also minimizes slippage of the device. The central ridge 26 lends rigidity that resists deformation of the pad and rupture of the adhesive layer under fluid pressure from the urethra, thereby enhancing the fluid-tight seal provided by the pad against the urethral meatus. It may be advantageous to extend the adhesive layer onto the labia-engaging surface 27, thereby further enhancing the stability of the device.

An incontinence device constructed in accordance with the first preferred female embodiment of the invention, as described above, can be made to withstand short-term fluid pressures from the urethra in the range of up to at least about 100, and preferably to about 170, centimeters of water without significant leakage. Pressures in this range are those that would typically result in involuntary urine voiding in cases of stress and urge incontinence, with 170 centimeters of water being the approximate maximum bear-down pressure for a typical adult human female.

As an option, the foam material of the pad, and/or the adhesive surface, can be provided with a medically-active composition. An antibacterial or germicidal agent, such as silver oxide or silver azide may be used, for example.

Figure 9:
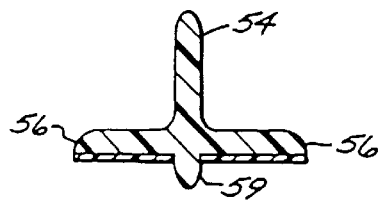
FIG. 9 is cross-sectional view taken along line 9—9 of FIG. 8.
Figure 10:
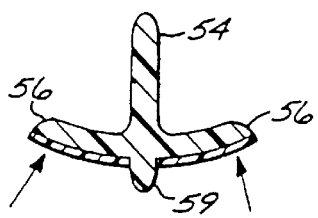
FIG. 10 is a cross-sectional view, similar to that of FIG. 9, showing the flexing of the lateral edges of the pad.
Figure 11:
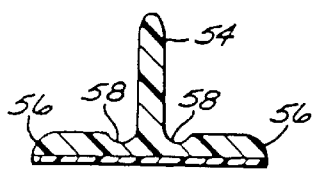
FIG. 11 is a cross-sectional view of a third modified form of the first preferred female embodiment.
Figure 12:
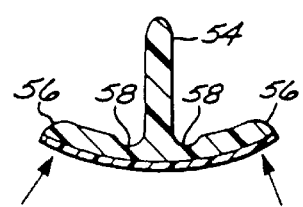
FIG. 12 is a cross-sectional view, similar to that of FIG. 11, showing the flexing of the lateral edges of the pad.

The first preferred embodiment lends itself to several modifications that may provide better comfort for certain individuals. For example. FIGS. 8, 9, and 10 show a modified device 50, which includes a pad 52 of substantially uniform thickness, except for a longitudinal ridge 54. This modification provides lateral edges 56 that flex more easily than those of the embodiment of FIGS. 1–7. Still greater flexibility may be provided by forming a longitudinal groove 58 on either side of the ridge 54, as shown in FIGS. 11 and 12.

As still another option, a short protuberance 59 may be provided on the base, as shown in FIGS. 9 and 10. The protuberance 59 serves as a locator for the urethral meatus, facilitating proper placement of the device. The protuberance 59 may also enhance the occlusion of the meatus.

Figure 17:
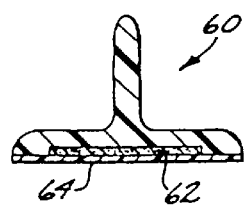
FIG. 17 is a cross-sectional view of a fourth modification of the first preferred female embodiment, wherein the pad includes a layer of super-absorbent material.
Figure 18:
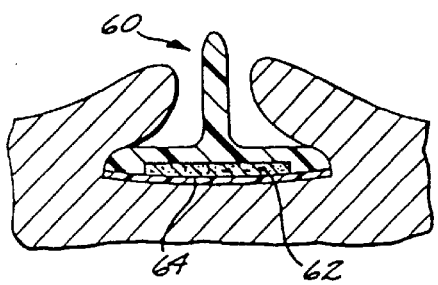
FIG. 18 is a cross-sectional view, similar to that of FIG. 17, showing the invention as installed in the external genitalia of a human female.
Figure 19:
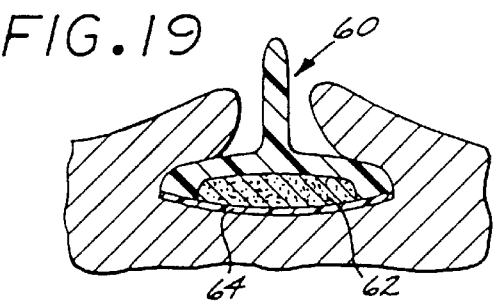
FIG. 19 is a cross-sectional view, similar to that of FIG. 18, showing the super-absorbent material after it has absorbed moisture.

Another modification of the first preferred female embodiment is shown in FIGS. 17, 18, and 19. As shown in these figures a modified device 60 includes a layer 62 of super-absorbent hydrophilic material adjacent the adhesive layer 64 on the base of the pad. The hydrophilic layer 62 is preferably a mixture of the PHEMA/PEG adhesive and a microsponge material, such as carboxymethylcellulose (CMC). The hydrophilic layer 62 draws moisture from the adhesive layer 64 and absorbs the moisture, thereby prolonging the useful lifetime of the adhesive by delaying saturation. Absorption of moisture causes the hydrophilic layer 62 to swell, as shown in FIG. 19, which may enhance the sealing properties of the device.

Figure 20:
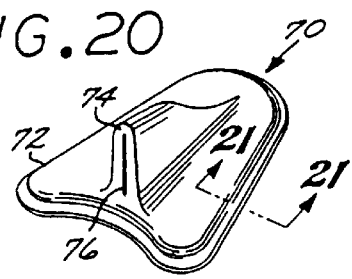
FIG. 20 is a perspective view of a fifth modified form of the first preferred female embodiment, which includes a finger hole.
Figure 22:
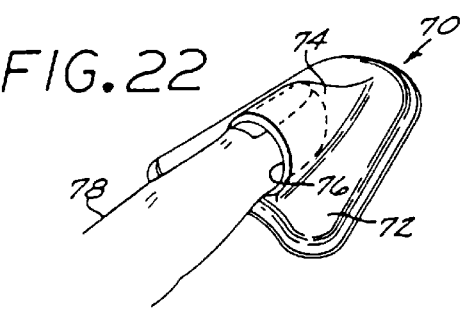
FIG. 22 is a perspective view, similar to that of FIG. 20, showing the device with a human finger inserted into the finger hole.
Figure 21:
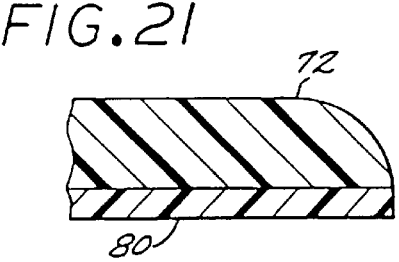
FIG. 21 is a cross-sectional view, taken along line 21—21 of FIG. 20.

Still another modification of the first preferred female embodiment is shown in FIGS. 20, 21 and 22. In these figures, a modified device 70 has a a pad 72 having an integral longitudinal ridge 74. The ridge 74 a finger hole 76 in its posterior edge. The finger hole 76 is normally in a collapsed state, as shown in FIG. 20. It expands to receive the user's finger 78, as shown in FIG. 22, to facilitate installation and removal.

Figure 23:
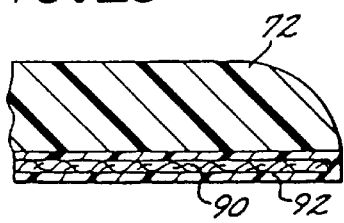
FIG. 23 is a cross-sectional view, similar to that of FIG. 21, showing a sixth modification of the first preferred female embodiment.

In FIG. 21, the device 70 is shown as having an adhesive layer 80 applied directly to the base of the pad 72, as previously described. FIG. 23 shows still another feature that can be incorporated, as a further modification, into any of the previously-described variations of the first preferred female embodiment. In this variation or modification, a scrim layer 90 is enclosed within the adhesive 92 applied to the base of the pad. The scrim layer 90 is preferably a thin, non-woven sheet of polyester that can reinforce an elastomeric material. In the present invention, the scrim layer 90 adds structural integrity to the adhesive material, thereby enhancing the durability of the device. As shown in FIG. 23, the scrim layer 90 is placed in the adhesive before the adhesive is cured to a semi-solid. Alternatively, the scrim layer 90 can be applied to the base of the pad before the adhesive is applied, in which case the scrim layer would be sandwiched between the adhesive and the base of the pad.

Figure 13:
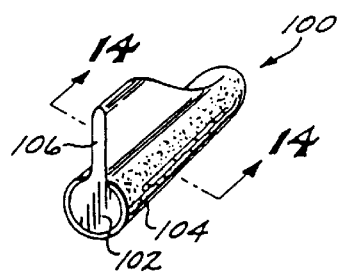
FIG. 13 is a perspective view of a second preferred female embodiment of the invention.
Figure 14:
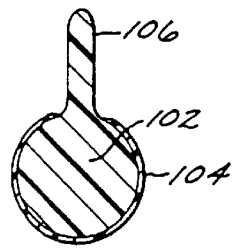
FIG. 14 is a cross-sectional view taken along line 14—14 of FIG. 13.
Figure 15:
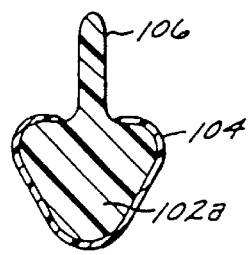
FIG. 15 is a cross-sectional view, similar to that of FIG. 14, showing a modified form of the second preferred female embodiment.
Figure 16:
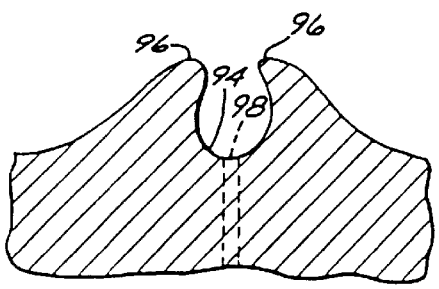
FIG. 16 is a cross-sectional view of the external female genitalia, showing a vestibule of the configuration for which the second preferred female embodiment is adapted.

It has been noted that some potential users of the present invention have a relatively narrow vestibule floor. This type of anatomical structure is shown in FIG. 16, which shows a simplified cross-sectional view of external female genitalia, wherein the vestibule floor 94 and the labia minora 96 define a relatively narrow space proximate the urethral meatus 98. For those with this type of anatomical structure, the above-described first preferred female embodiment may be uncomfortable, or altogether unsuitable. Consequently, a second preferred female embodiment, illustrated in FIGS. 13, 14, and 15, is contemplated for such users.

In accordance with this second preferred female embodiment, a female urinary incontinence device 100 includes substantially tubular pad 102, substantially the entire exterior surface of which is coated with an adhesive 104, of a type described above. The pad 102 has a longitudinal ridge 106, preferably not coated with the adhesive, that is used as a gripping element to facilitate installation and removal. As shown in FIGS. 13 and 14, the tubular pad may have a substantially elliptical cross-section. Alternatively, as shown in FIG. 15, a pad 102a, having a cross-sectional shape similar to a rounded triangle, may be more suitable for some users.

Figure 24:
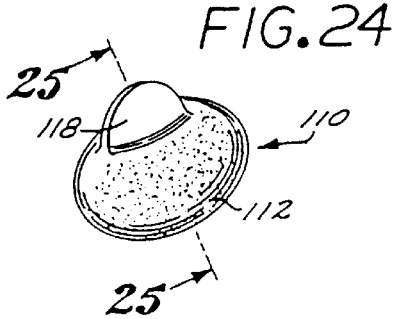
FIG. 24 is a perspective view of a third preferred female embodiment of the invention.
Figure 25:
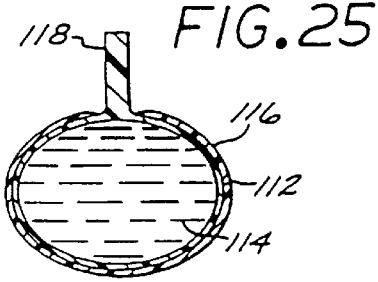
FIG. 25 is a cross-sectional view taken along line 25—25 of FIG. 24.
Figure 26:
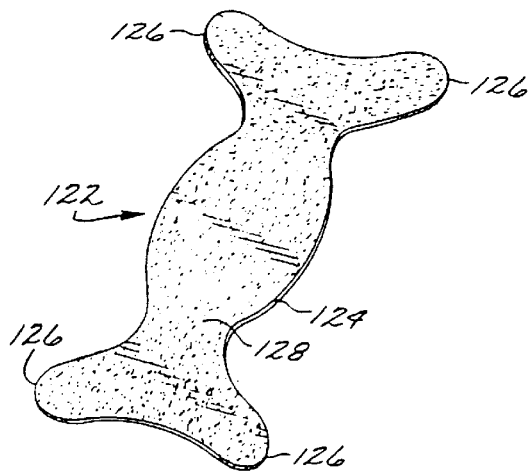
FIG. 26 is a perpective view of a first preferred male embodiment of the invention.
Figure 27:
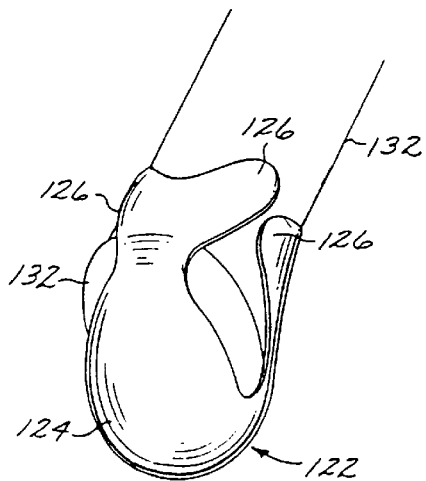
FIG. 27 is a perspective view, showing the embodiment of FIG. 26 attached to the glans of a penis.

FIGS. 24 and 25 illustrate a third preferred female embodiment of the invention. A urinary incontinence device 110, in accordance with this embodiment, includes a thin, elastomeric shell or bladder 112, formed of polyurethane or a similar thin, resilient, elastomeric material. The bladder 112 is filled with a suitable biocompatible liquid or gel 114 by means of a needle, and the needle hole is then sealed, thereby forming a compliant sac. A preferred material for filling the sac is a hydrogel, similar the hydrogel adhesives described above. Substantially the entire exterior surface of the sac is coated with an adhesive 116, of a type described above.

In use, the device 110 is inserted under the labia minora so as to be seated against the floor of the vestibule, occluding the urethral meatus. The sac conforms to the anatomical structure of the external female genitalia, filling the interlabial space, and sealing against the urethral meatus with the aid of the adhesive. Because the sac is so compliant, it can be used for a wide variety of anatomical structures, providing high levels of comfort. The device may advantageously be provided with a raised tab 118, not coated with the adhesive, to be gripped by the user, to facilitate the installation and removal of the device 110.

FIGS. 26 through 30 illustrate several embodiments of the invention suitable for use by male patients. A male urinary incontinence device, in accordance with the embodiment of FIGS. 26 and 27 comprises a thin, flexible, resilient pad 122, which may be formed from any of the above-described materials used for the pads of the female embodiments of FIGS. 1 through 23. The pad 122 has a generally elliptical central portion 124, with a pair of laterally extending tabs 126 at each end. The pad has an inner surface which is provided with a pressure-sensitive hydrophilic hydrogel adhesive layer 128, which may be formed in any of the manners described above. The pad 122 conforms to the glans 130 of a patient's penis 132, and it is removably retained thereon by means of the adhesive layer 128, whereby the adhesive also seals against and occludes the urethral meatus (not shown). The generally elliptical central portion 124 engages against the urethral meatus, and provides the sealing and occlusion functions. The laterally-extending tabs 126 are wrapped around the distal portion of the shaft of the penis 132 for adhesively securing the pad 122 in place.

Figure 28:
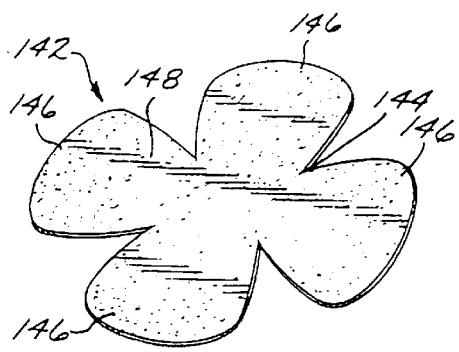
FIG. 28 is a perspective view of a second preferred male embodiment of the invention.
Figure 29:
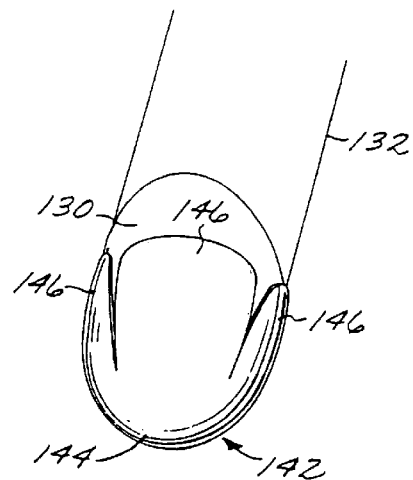
FIG. 29 is a perspective view, showing the embodiment of FIG. 28 attached to the glans of a penis.

In the embodiment of FIGS. 28 and 29, a male urinary incontinence device comprises a pad 142 that has a central sealing and occluding portion 144 with a plurality of radially-extending tabs 146 for adhesively securing the device to the glans 130. Again, the inner surface of the pad 142 is provided with a layer 148 of the above-described adhesive.

Figure 30:
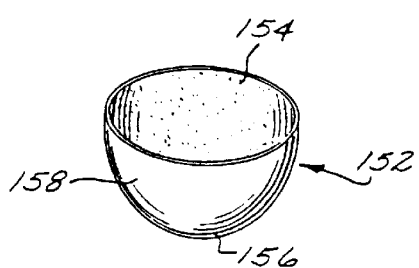
FIG. 30 is a perspective view of a third preferred male embodiment of the invention.

In accordance with the embodiment of FIG. 30, a male urinary incontinence device comprises a pad 152 that is in the configuration of a generally hemispherical cap that conforms to and covers a substantial portion of the glans 130. Again, the inner surface of the pad 152 is provided with a layer 154 of the above-described adhesive. In this embodiment, the pad 152 has a central portion 154 that engages against the urethral meatus, and a peripheral portion, integral with and extending from the central portion 156, that is removably attached by the adhesive layer 154 to the glans 130.

As with the female embodiments, the pad of the male embodiments can be coated or impregnated with a medically active compound, such as an anti-bacterial or germicidal agent. Alternatively, the compound can be incorporated into the adhesive.

From the foregoing, the advantages of the present invention will be readily appreciated. The incontinence device in accordance with the present invention provides effective management of urinary incontinence, especially stress and urge incontinence, without the inconvenience and discomfort associated with prior art urine collection devices and absorbent pads. The present invention is easy to use and comfortable to wear. It is easily shaped and sized to fit each individual user's anatomy with optimum effectiveness and comfort. Easily and inexpensively manufactured, it can be made as a disposable item.

While several preferred embodiments and modifications thereof have been described above, it should be understood that still further modifications and variations will suggest themselves to those skilled in the pertinent arts. Such variations and modifications should be considered within the spirit and scope of the invention, as defined in the claims that follow.

What is claimed is:

1. A device for controlling urinary incontinence in a male user, said male user having a urethra and external genitalia which includes a penis with a glans, said urethra exiting the glans at an opening which is a urethral meatus, said device comprising:
    a body comprising a pad, a portion of which is conformable to the glans so as to occlude the urethral meatus, said body having a surface that in use engages the external genitalia of the male user, said pad comprising:
       a body comprising a pad, a portion of which is conformable to the glans as to occlude the urethral meatus, said body having a surface that in use engages the external genitalia of the male user, said pad comprising:
          a central portion that in use engages against the urethral meatus; and
          a peripheral portion adjacent to the central portion, said peripheral portion being configured to secure the pad to the penis wherein said peripheral portion comprises a pair of tabs extending in opposite directions from the central portion,
       an adhesive disposed on said surface, and
       said body and said adhesive being constructed to be conformable to the external genitalia of the user so as to, in use, cause said surface to sealingly engage the external genitalia and occlude the urethral meatus, thereby to substantially block the flow of urine from the urethral meatus.

2. A device for controlling urinary incontinence in a male user, said male user having a urethra and external genitalia which includes a penis with a glans, said urethra exiting the glans at an opening which is a urethral meatus, said device comprising:
    a body comprising a pad, a portion of which is conformable to the glans so as to occlude the urethral meatus, said body having a surface that in use engages the external genitalia of the male user, wherein the pad comprises a substantially hemispherical cap said pad comprising:
       a central portion of said hemispherical cap that in use engages against the urethral meatus; and
       a peripheral portion adjacent to the central portion, said peripheral portion being configured to secure the pad to the penis, said peripheral portion being integral with and extending from the central portion;
    an adhesive disposed on said surface, and
    said body and said adhesive being constructed to be conformable to the external genitalia of the user so as to, in use, cause said surface to sealingly engage the external genitalia and occlude the urethral meatus, thereby to substantially block the flow of urine from the urethral meatus.

3. A device for controlling urinary incontinence by the occlusion of the urethral meatus in the glans of the penis of a human male patient, comprising:
    a resilient pad that is configured to be engageable with the glans, the pad having a surface which includes a central portion that in use engages against the urethral meatus,
    an adhesive disposed on said surface of said central portion, and
    said pad and said adhesive being constructed to be conformable to the glans so as to, in use, cause said surface to sealingly engage the glans and occlude the urethral meatus to substantially block the flow of urine therefrom, and
    a plurality of tabs extending radially from the central portion and configured to be attached to the penis.

4. The device of claim 3, wherein the adhesive comprises a mixture of about 45% to about 75% poly 2-hydroxyethyl methacrylate and about 55% to about 25% polyethylene glycol, and wherein the poly 2-hydroxyethyl methacrylate comprises a mixture of about 10% to about 50% poly 2-hydroxyethyl methacrylate having a molecular weight between about 10,000 and about 100,000, and about 90% to about 50% poly 2-hydroxyethyl methacrylate having a molecular weight greater than about 100,000.

5. The device of claim 3 wherein the adhesive includes poly 2-hydroxyethylmethacrylate and a plasticizer selected from polyethylene glycol, propylene glycol, polypropylene glycol, and glycerin.

6. The device of claim 3 wherein the adhesive is a mixture of polyethylene glycol and poly-2-hydroxyethyl methacrylate.

7. The device of claim 3 wherein the adhesive includes a medically active compound.

8. The device of claim 3 wherein the pad is made of a biocompatible foam material.

9. The device of claim 8 wherein the foam material is formed from the water actuation of a prepolymer selected from the group consisting of toluene diisocyanate and methylene diphenyl diisocyanate.

10. The device of claim 9 wherein the adhesive is formed by reacting the prepolymer with ammonium hydroxide during the water actuation thereof.

11. A device for controlling urinary incontinence in a human male, comprising:

a body having a surface that in use engages the glans of the penis, an adhesive disposed on said surface, said body and said adhesive being constructed to be conformable to the glans so as to, in use, cause said surface to sealingly engage the glans and occlude the urethral meatus, thereby to substantially block the flow of urine from the urethral meatus, and a tab extending from said body that in use engages the shaft of the penis, a portion of said tab being adhesive.

12. The device of claim 11, wherein the device includes a pair of tabs that extend from said body in opposite directions.

13. The device of claim 11 wherein the device includes a plurality of tabs that extend from said body.

14. The device of claim 13 wherein the device includes a plurality of tabs that extend radially from said body.

15. A device for controlling urinary incontinence in a human male, comprising:

a body comprising a generally hemispherical cap, said body having a surface that in use engages the glans of the penis, an adhesive disposed on said surface, and said body and said adhesive being constructed to be conformable to the glans so as to, in use, cause said surface to sealingly engage the glans and occlude the urethral meatus, thereby to substantially block the flow of urine from the urethral meatus.

* * * * *